(12) United States Patent
Sakaguchi (10) Patent No.: US 8,663,187 B2
(45) Date of Patent: Mar. 4, 2014

(54) FEMALE MEMBER FOR HOOK-AND-LOOP FASTENER, HOOK-AND-LOOP FASTENER EMPLOYING THE FEMALE MEMBER, AND ABSORBENT ARTICLE EMPLOYING THE HOOK-AND-LOOP FASTENER

(75) Inventor: Satoru Sakaguchi, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 504 days.

(21) Appl. No.: 12/920,845

(22) PCT Filed: Mar. 5, 2009

(86) PCT No.: PCT/JP2009/054197
§ 371 (c)(1),
(2), (4) Date: Jan. 30, 2011

(87) PCT Pub. No.: WO2009/110564
PCT Pub. Date: Sep. 11, 2009

(65) Prior Publication Data
US 2011/0118692 A1    May 19, 2011

(30) Foreign Application Priority Data
Mar. 6, 2008    (JP) .................................. 2008-056903

(51) Int. Cl.
*A61F 13/15*    (2006.01)

(52) U.S. Cl.
USPC ........... 604/396; 604/391; 604/387; 604/386; 604/394

(58) Field of Classification Search
USPC .......................... 604/396, 391, 387, 386, 394
See application file for complete search history.

(56) References Cited

U.S. PATENT DOCUMENTS

2009/0068394 A1    3/2009    Noelle et al.

FOREIGN PATENT DOCUMENTS

| JP | 06033359 A | 2/1994 |
| JP | 11061624 A | 3/1999 |
| JP | 11152669 A | 6/1999 |
| JP | 11302963 A | 11/1999 |
| JP | 11335960 A | 12/1999 |
| JP | 2005160967 A | 6/2005 |
| JP | 2007268219 A | 10/2007 |
| JP | 2008029762 A | 2/2008 |
| WO | 2006008662 | 1/2006 |
| WO | 2007093685 | 8/2007 |

OTHER PUBLICATIONS

Office Action issued on Nov. 7, 2012 by the Egyptian Patent Office in corresponding Egyptian Application No. 2010091494, with English translation.

(Continued)

*Primary Examiner* — Jacqueline F Stephens
(74) *Attorney, Agent, or Firm* — Lowe Hauptman & Ham, LLP (57) ABSTRACT

A female member for a hook-and-loop fastener is provided. Even when the hook-and-loop fastener part is deformed or an instantaneous impact peel force is applied to the fastener part, the female member does not peel off the male member. When the male member is peeled from the female member, no fluffing caused by shedding of a fibrous material occurs. The female member for a hook-and-loop fastener is constituted of a fibrous material and can engage with a mating male member. The female member is composed of: dense fiber portions arranged in rows and having a high density of the fibrous material; and sparse fiber portions arranged in rows alternately with these dense fiber portions and having a lower density of the fibrous material than the dense fiber portions. The dense fiber portions deform elastically, and this prevents undesirable peeling and diminishes fluffing.

10 Claims, 10 Drawing Sheets

(56) References Cited

OTHER PUBLICATIONS

Extended European Search Report for Application No. 09718501.1 mailed Mar. 29, 2012.
International Search Report for PCT/JP2009/054197 issued Apr. 7, 2009.
Office Action corresponding to JP 2008-056903, dated Oct. 2, 2012.
Office Action issued on Mar. 7, 2013 for counterpart Colombian Patent Application File No. 10 123356.
Office Action issued Oct. 1, 2013, corresponds to GC patent application No. 2009/12976.

FEMALE MEMBER FOR HOOK-AND-LOOP FASTENER, HOOK-AND-LOOP FASTENER EMPLOYING THE FEMALE MEMBER, AND ABSORBENT ARTICLE EMPLOYING THE HOOK-AND-LOOP FASTENER

RELATED APPLICATIONS

The present application is a national phase of PCT/JP2009/054197, filed Mar. 5, 2009, and claims priority from, Japanese Application Number 2008-056903, filed Mar. 6, 2008.

TECHNICAL FIELD

The present invention relates to a female member of a hook-and-loop fastener, a hook-and-loop fastener employing the female member, and an absorbent article employing the hook-and-loop fastener, such as a disposable paper diaper, a sanitary napkin, a pantiliner or incontinence pad.

BACKGROUND ART

An absorbent article, such as a paper diaper, is designed to be developed using a hook-and-loop fastener so as to be attachable to and detachable from a human body. The hook-and-loop fastener includes a female member and a male member, and these members are mutually connected to and separated from each other by engagement and disengagement therebetween. In the male member, an engagement surface including a group of multiple projections (hooks) is formed, while the female member employs a nonwoven with which the group of projections can engage. Patent Literatures 1 to 3 disclose conventional examples of a female member in a hook-and-loop fastener.

Patent Literature 1 (JP-A 11-335960) discloses a female member employing an embossed air-through nonwoven whose main fiber has a length of 30 mm to 100 mm. Specifically, the nonwoven is embossed in a direction which intersects with a MD direction across the entire width to have an elongation percentage of 75% or less when weighted in a CD direction by 2N/25 mm, and a thickness of 0.4 mm or more. The fibers constituting the air-through nonwoven form a layer structure in which the fibers are basically two-dimensionally arranged to form each layer, and in which the fibers are fused to be bonded with one another. In other words, the embossing is performed in a pattern that intersects with the MD direction in which a number of fibers are arranged. Thereby, the fiber layers are fused and integrated to strengthen the connection between the fibers and to make the fibers less fluffy.

Patent Literature 2 (JP-A 06-33359) discloses a female member made in a following manner. Specifically, a spunbonded nonwoven is placed on a heat-shrinkable fabric web and integrated therewith, and thereafter the fiber web is contracted by thermal processing to form 2 to 40 wrinkles per $cm^2$ on the spunbonded nonwoven, the wrinkles each having a depth of 0.2 mm to 3 mm. In the spunbonded nonwoven, endless fibers two-dimensionally arranged are securely fused by thermal embossing or the like. Accordingly, the spunbonded nonwoven has a characteristic of being unlikely to be fluffy. When the heat-shrinkable fiber web having its lower layer side integrated with the spunbonded nonwoven is thermally contracted, a number of wrinkles are formed in the spunbonded nonwoven, and the wrinkles allow the female member to engage with the female member.

Patent Literature 3 (JP-A 11-152669) discloses that loops of a fiber bundle are formed in a heat-nonshrinkable fiber layer in the following manner. Specifically, a heat-shrinkable fiber layer is stacked on the heat-nonshrinkable fiber layer, and then a high-pressure fluid is ejected onto the layered body to interlace the fibers with one another while rearranging the fibers so as to obtain a perforated nonwoven. Thereafter, the heat shrinkable fiber layer is contracted with a thermal treatment to form the loops of a fiber bundle in the heat-nonshrinkable fiber layer. With such processes, curled objects projecting in random directions are formed.

DISCLOSURE OF THE INVENTION

In Patent Literature 1, connections of fibers are caused to extend in all directions on a plane of a nonwoven by thermal fusion bonding, and the fibers are further strongly integrated by embossing. Accordingly, the nonwoven has large engagement force with a male member and is less fluffy. On the other hand, the nonwoven loses its elasticity in a release direction of the engagement. For this reason, when a hook-and-loop fastener is deformed while a diaper or the like is putted on, or when an instantaneous impulsive force for peeling acts on the hook-and-loop fastener, the female member is easily peeled off from the male member.

Patent Literature 2, in which a behavior similar to that of Patent Literature 1 is displayed, has similar problems.

Patent Literature 3 does not have problems as those in Patent Literatures 1 and 2 because loops of a fiber bundle are formed, and because fibers of an entire nonwoven is loosely connected by fiber interlacing. However, on the other hand, since the fibers are loosely connected by fiber interlacing, there exists a problem that the nonwoven is fluffy because fibers are easily fallen off when the male member is peeled off from engagement. However, if fiber interlacing is intensified to address this problem, the entire nonwoven is too tightened to generate loops of a fiber bundle by thermal contraction so that the male member is less likely to be caught by the female member.

In this regard, an object of the present invention is to provide a female member of a hook-and-loop fastener, which does not easily come off from a male member even if a hook-and-loop portion is deformed or instantaneous impulsive force for peeling acts thereon, and furthermore will not allow a fibrous material to fall off and thus will not be fluffy when the male member is peeled off, and also to provide a hook-and-loop fastener using the female member, and an absorbent article using the hook-and-loop fastener.

According to an invention of claim 1, there is provided a female member of a hook-and-loop fastener formed of a fibrous material, the female member engageable with a mating male member, the female member comprising: a plurality of lines of dense fiber portions in which the fibrous material has a high basis weight; and a plurality of lines of sparse fiber portions provided between the dense fiber portions, the fibrous material in the sparse fiber portions having a basis weight lower than in the dense fiber portions.

According to an invention of claim 2, there is provided the female member of a hook-and-loop fastener according to claim 1, wherein the dense fiber portions are convex ribs which are formed of the fibrous material being piled up, and the sparse fiber portions are concave grooves provided between the ribs.

According to an invention of claim 3, there is provided the female member of a hook-and-loop fastener according to claim 2, wherein each of the ribs has a thickness of 0.3 mm to 0.6 mm, and a pitch between the lines of the ribs is 2 mm to 15 mm.

According to an invention of claim 4, there is provided the female member of a hook-and-loop fastener according to claim 2 or 3, wherein the fibrous material is piled on a base layer portion having a thickness of the fibrous material underlying the grooves so as to form the ribs, and a volume of the fibrous material piled on the base layer portion is equivalent to a volume inside the grooves.

According to an invention of claim 5, there is provided the female member of a hook-and-loop fastener according to any one of claims 1 to 4, wherein the sparse fiber portions have a plurality of apertures passing through from a front surface to a back surface formed to be arrayed in a line direction of the ribs.

According to an invention of claim 6, there is provided the female member of a hook-and-loop fastener according to any one of claims 1 to 5, wherein the fibrous material continues from a back surface side to a front surface side in a thickness direction of the fibrous material in a state where fibers constituting the fibrous material interlaced with one another.

According to an invention of claim 7, there is provided a hook-and-loop fastener, comprising: a male member including an engagement surface formed of groups of a plurality of projection; and the female member according to claims 1 to 6, engageable with the engagement surface.

According to an invention of claim 8, there is provided an absorbent article which is formed of an outer member including a front waistline member, a back waistline member, and an inseam member, and of an absorber integrally provided to the inseam member, the absorbent article comprising: a hook-and-loop fastener formed of a male member and the female member according to claims 1 to 7, the male member being provided to at least one of the front waistline member and the back waistline member and including an engagement surface, the female member according to claims 1 to 7 being provided to the other one of the front waistline member and the back waistline member and engageable with the engagement surface.

According to an invention of claim 9, there is provided the absorbent article according to claim 7, edge portions on both sides of the front waistline member are respectively joined to edge portions on both sides of the back waistline member, in advance, by joining hook-and-loop fasteners arranged on the edge portions on the both sides of the front waistline member and the edge portions on the both sides of the back waistline member in advance, which causes the absorbent article to have an underpants shape as a whole.

According to an invention of claim 10, there is provided an absorbent article which is formed of an outer member including a front waistline member, a back waistline member, and an inseam member, and of an absorber which is integrally provided to the inseam member, wherein at least one of the front waistline member and the back waistline member is formed of the female member of a hook-and-loop fastener according to claims 1 to 6.

According to the present invention, elastic deformation in which a height is increased as a width is narrowed is caused when a dense fiber portion in which a fibrous material has a high basis weight is elongated in a thickness direction. Accordingly, engagement with a male member gains stickiness, which results in preferable engagement with the male member. For this reason, even if a hook-and-loop fastener is deformed or impulsive force for peeling acts thereon, a female member can be prevented from being peeled off form the male member. Furthermore, the fibrous material does not come off, and is prevented from being fluffy.

The present invention will be described below in detail by referring to the drawings.

Figure 1:
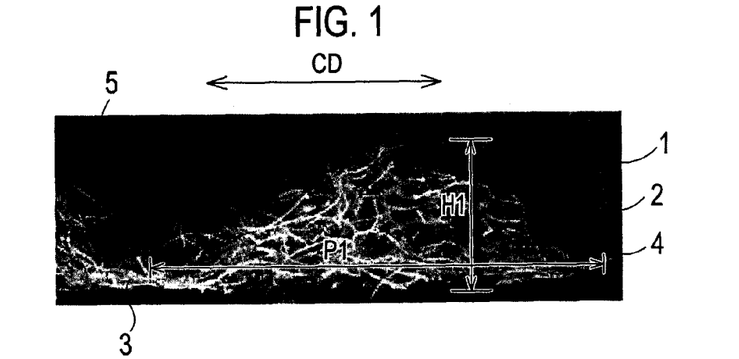
FIG. 1 is a cross-sectional view showing a female member according to one embodiment of the present invention and a cross-sectional view taken along the A-A line in FIG. 2.
Figure 2:
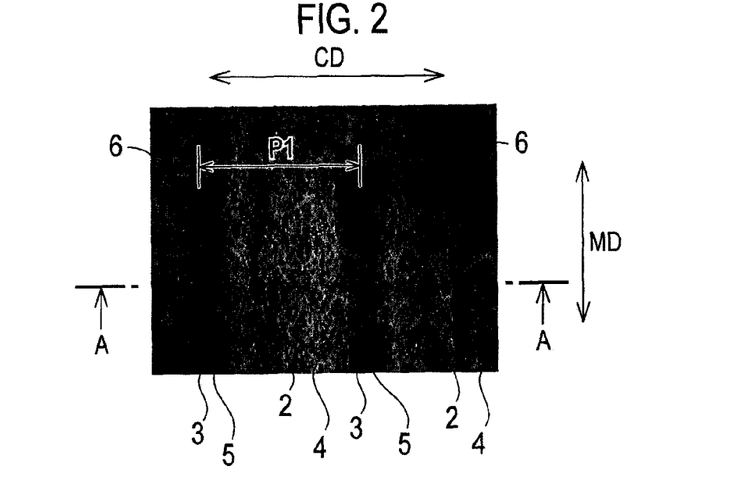
FIG. 2 is a plan view showing a front surface of the female member according to one embodiment.
Figure 3:
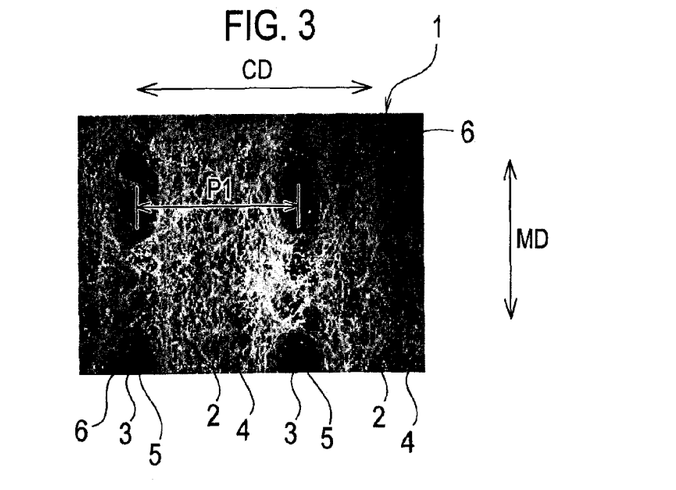
FIG. 3 is a bottom view showing a back surface according to one embodiment.

FIGS. 1 to 3 show a female member 1 of a hook-and-loop fastener in one embodiment of the present invention. The female member 1 is an air-through nonwoven having a number of fibrous materials as constituents, and is formed by fusing the fibrous materials with respect to each other by using hot blast. As shown in FIG. 1, the female member 1 includes a dense fiber portion 2 and a sparse fiber portion 3.

The dense fiber portion 2 is a portion in which the fibrous material has a high basis weight and the sparse fiber portion 3 is a portion in which the fibrous material has a low basis weight. The basis weight is a weight (amount) of the fibrous material per unit area, and is expressed by, for example, a unit of $g/m^2$. The dense fiber portion 2 and the sparse fiber portion 3 extend in an MD direction (conveyance direction in a manufacturing process) to form belt-like shapes. In addition, the dense fiber portion 2 and the sparse fiber portion 3 are arranged in multiple lines in a CD direction (direction perpendicular to the conveyance direction in the manufacturing process). Each of lines of the sparse fiber portions 3 is positioned between two lines of the dense fiber portions 2. That is, the dense fiber portions 2 and the sparse fiber portions 3 are alternately positioned in the CD direction. Note that, when the dense fiber portions 2 and the sparse fiber portions 3 are alternately arranged, the arrangement includes that a dense fiber portion, a sparse fiber portion, a sparse fiber portion, and a dense fiber portion are arranged in this order and a sparse fiber portion, a dense fiber portion, a dense fiber portion, and a sparse fiber portion are arranged in this order.

As will be described later, the dense fiber portion 2 is a portion in which the fibrous material is piled by using the hot blast and forms a convex rib portion 4. The sparse fiber portion 3 is a portion in which the fibrous material is removed by the hot blast and forms a concave groove 5. These rib portion 4 and groove portion 5 continue in the MD direction and are alternately arranged in the CD direction. A fibrous material constituting the rib portion 4 forms a fiber assembly in the rib portion 4. In addition, the most part of the fibrous material constituting one rib portion 4 is independent from an adjacent rib portion 4. The rib portion 4 is formed by piling the fibrous material on a base layer portion 7 consisted of the thickness of the fibrous material under the groove 5. An amount of the fibrous material piled on the base layer portion 7 equals to the fibrous material equivalent to an amount in the groove 5. That is, the dense fiber portion 2, which is the rib portion 4, is formed by piling, on both sides of the groove 5, the fibrous material removed by the hot blast when the sparse fiber portion 3 on the lower side of the groove 5 is formed.

Note that, as shown in FIG. 2 and FIG. 3, some fibrous materials in one rib portion 4 are connected with the adjacent rib portion 4 in a base portion (base layer portion 7) of the rib portion 4. This connection allows the female member 1 to keep the form of a nonwoven sheet.

As shown in FIG. 2 and FIG. 3, the groove 5 (sparse fiber portion 3) has an aperture 6 formed therein. The aperture 6 is formed so as to pass through both sides of the female member 1. The aperture 6 is formed by removing the fibrous material by using the hot blast. With the formation of the aperture 6 in the groove 5, the fibrous material can come closer to the rib portion 4 by the aperture 6. Accordingly, the basis weight the rib portion 4 can be increased. Thereby, engagement force of the rib portion 4 with an unillustrated male member can be increased, which results in stable engagement of the rib portion 4 with the male member. In addition, as shown in FIG. 3, the fibrous material in the periphery of the aperture 6 tends to direct in the CD direction. Accordingly, a stretch ratio of the sheet in the CD direction is improved. Note that, the aperture 6 may be formed or may not be formed.

In this embodiment, as shown in FIG. 1, the rib portion 4 is formed on the front surface side, while the back surface side is flat. However, the rib portion 4 may be formed on both sides of the front and back surfaces.

In addition, in the foregoing embodiment, the rib portion 4 is formed in such a manner that the fibrous material removed by the hot blast is piled on both sides of the groove 5. However, the groove 5 may be formed by removing the fibrous material by embossing the front surface with a comb-like item to remove the fibrous material and the rib portion 4 may be formed by shifting the fibrous material removed from the groove 5 to the both sides of the groove 5.

Next, conditions, such as a size and a material, for the female member 1 will be described.

The basis weight of the total nonwoven consisting of the female member 1 is preferably 15 to 100 g/m$^2$, and more preferably 20 to 50 g/m$^2$. If the basis weight is less than 15 g/m$^2$, a difference between the basis weight of the rib portion 4 and that of the groove 5 have to be small. Otherwise, the fibrous material of the groove 5 becomes excessively less, which causes a lack of strength in the CD direction. On the other hand, it is not preferable that the basis weight exceed 100 g/m$^2$ because the cost is increased.

A pitch P1 between the lines of the rib portions 4 (see, FIG. 2 and FIG. 3) is 2 mm to 15 mm, and more preferably 3 mm to 10 mm. If the pitch P1 is less than 2 mm, the rib portions 4 cannot be uniformly formed within the above-described basis weight. This is because the rib portion 4 is formed by removing the fibrous material. On the other hand, in a case where the pitch P1 exceeds 15 mm, when a width of the groove 5 is set to be small (for example, 1 to 2 mm), the rib portion 4 is widened, whereas the height of the rib portion 4 is lowered. Thus, the rib portion 4 cannot be smoothly engaged with the male member. In addition, when the width of the groove 5 is increased (for example, 5 to 6 mm), an engagement area with the male member is decreased, and engagement force becomes deficient.

A thickness H1 of the rib portion 4 (see, FIG. 1), that is, a thickness of the nonwoven, is 0.3 mm to 6 mm. If the thickness H1 is less than 0.3 mm, the rib portion 4 is less likely to be hooked by the male member and an elastic deformation effect of the rib portion 4 cannot be obtained. If the thickness H1 exceeds 6 mm, the female member 1 becomes excessively high bulk, and becomes inconvenient for handling.

As the fibrous material to be used for the nonwoven, which is the female member 1, a composite fiber having a core-in-sheath structure is selected. This composite fiber is formed of a resin having a sheath component with a lower melting point than a resin constituting a core component. Compounding ratios of these resins are preferably 50% or more, and more preferably 100%. Note that, it is not preferable that another fiber formed of a material having a higher melting point than the sheath component be mixed because it leads deterioration in the strength of the entire nonwoven and causes the fibers to fall off. However, for example, it is possible that a high crimp type fiber is mixed to make the female member 1 high bulk or a stretching elastic yarn for a purpose of storing elastic deformation of the rib portion 4 is mixed.

As the fibrous material, the composition of the core component and the sheath component includes compositions of, for example, PP (polypropylene) and PE (polyethylene), PP and low-melting-point PP, PET (polyethylene terephthalate) and low-melting-point PET, PET and PE. However, the composition is not limited thereto. As a fiber to be mixed to the fibrous material, a fiber which has a good compatibility with the sheath component resin of the fibrous material is selected. For example, a fiber such as rayon, PET, PP, polyamide such as nylon, acryl, urethane, or cotton can be selected. In addition, a fiber is not limited to this, but any material can be selected as long as the material can form a web by being mixed into the fibrous material.

A thickness of the fibrous material is 1 to 15 dtex, and preferably 1.5 to 9 dtex. If the thickness is less than 1 dtex, the strength of a single yarn is too low, and thus the fiber is easily broken when engaged with the male member. This makes it difficult for a web to be formed by a card. Accordingly, productivity is decreased. If the thickness exceeds 15 dtex, a texture is deteriorated and the number of fibers per unit weight is decreased. Accordingly, the engagement strength with the male member is extremely decreased.

A length of the fibrous material to be used is 25 mm to 100 mm, and more preferably, 30 mm to 60 mm. If the length is less than 25 mm, the fiber is too short, which causes the fibrous material to be fluffy. On the other hand, if the length exceeds 100 mm, it becomes difficult to form a web by a card. Accordingly, productivity is decreased.

In the female member 1 having above-mentioned configuration, the fibrous material of the groove 5 is added to the rib portion 4, and thus the rib portion 4 is high in fiber and is high bulk. For this reason, the engagement with the male member becomes preferable. In addition, the fibrous material of the rib portion 4 constitutes the rib portion 4 in such a way that the fibrous material located in the groove 5 is blown off by air-jet. Thus, the fibrous material constituting the rib portion 4 has a random fiber orientation in relation to the MD direction, the CD direction, as well as the thickness direction. Accordingly, the fibrous material has large engagement stickiness, and thus has excellent engagement and less fluffy. In contrast, in the structure in which the fibrous materials are connected with each other by thermal fusion, there is a problem in that the engagement stickiness is lowered and the engagement characteristic is decreased, even though the structure can prevent the fibrous materials from being fluffy.

Figure 4:
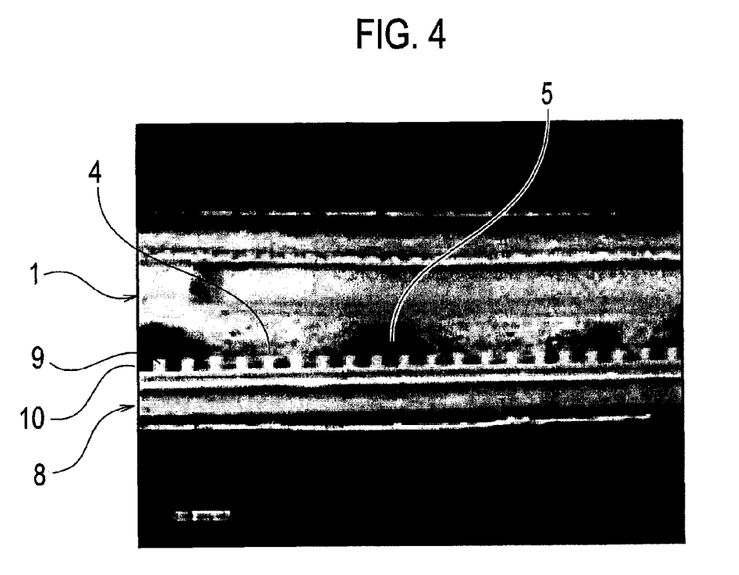
FIG. 4 is a cross-sectional view showing an engagement state of the female member with male member according to one embodiment.
Figure 5:
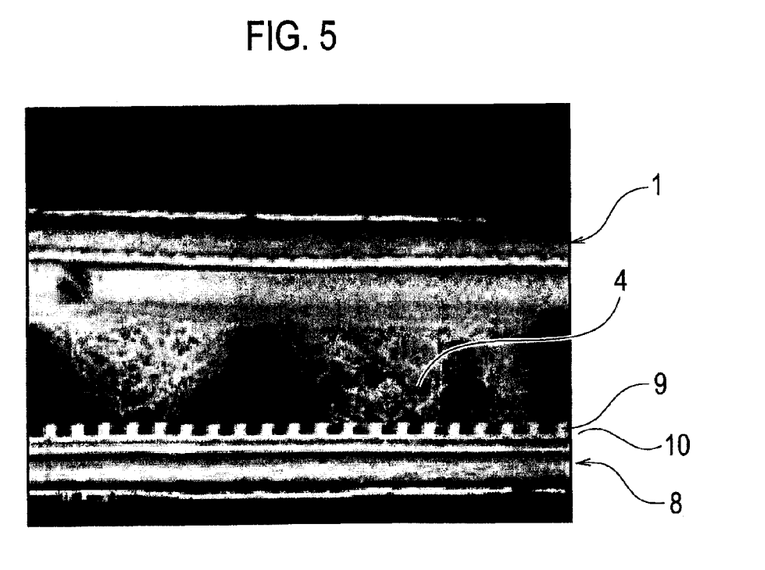
FIG. 5 is a cross-sectional view showing a peeled off state from the state of FIG. 4.

FIG. 4 and FIG. 5 show a state where the female member 1 according to the present embodiment is engaged with the male member 8. FIG. 4 shows an engaged state and FIG. 5 shows a peeled-off state. The male member 8 includes an engagement surface 10 having multiple projections 9. This engagement surface 10 faces to the female member 1. The female member 1 and the male member 8 are approximated with each other so that the projections 9 engage with the fibrous material of the rib portion 4. At this time, the groove 5 may be engaged or may not be engaged.

In the peeled-off state in FIG. 5, a most part of the fibrous material constituting the rib portion 4 is separated from the adjacent rib portion 4. Accordingly, a vertex of each rib portion 4 is pulled in the thickness direction. When peeled off, the rib portion 4 causes an elastic deformation in which the rib portion 4 increases the height thereof while decreasing the width thereof. The rib portion 4 engaged stretching in this way can absorb shocks which act by bending or instantaneous impact force generated by an abdominal pressure. Accordingly, the female member 1 is not peeled off from the engaged state with the male member 8.

Figure 6:
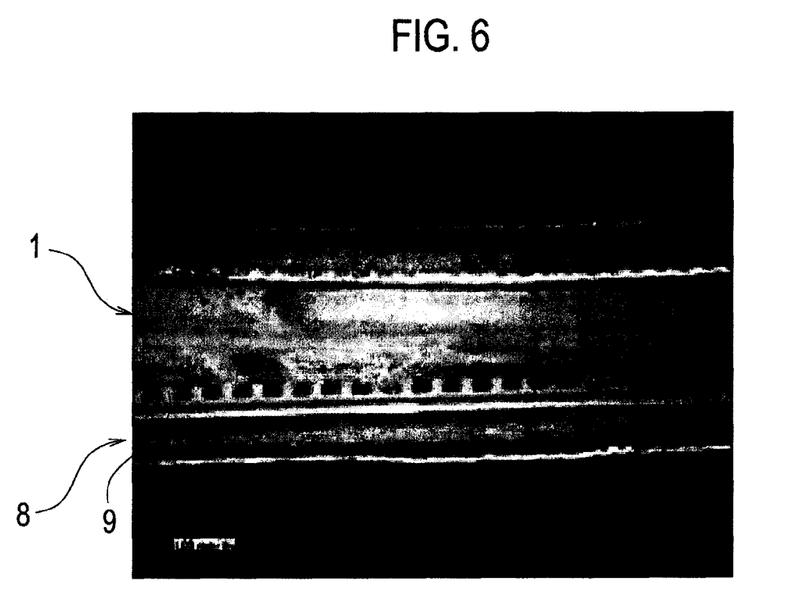
FIG. 6 is a cross-sectional view showing an engagement state when the back surface of the female member is set to be an engagement surface.
Figure 7:
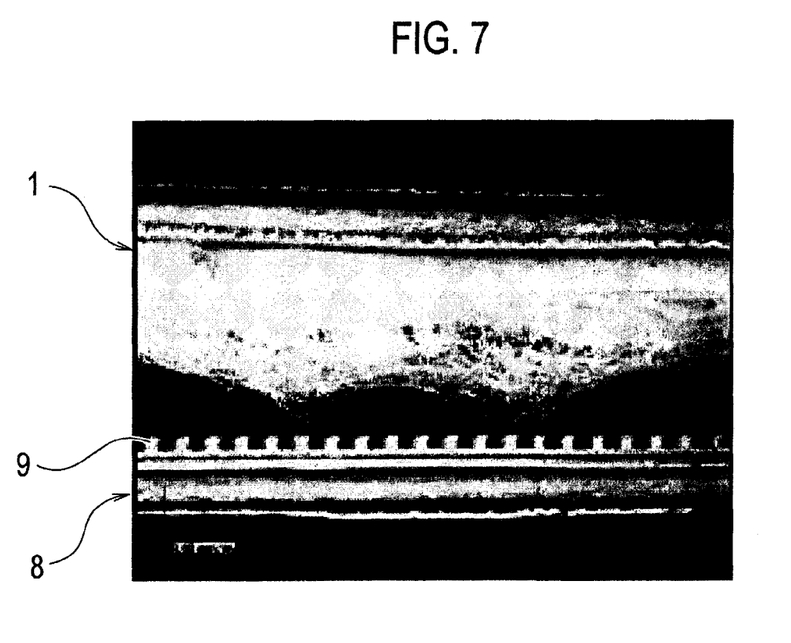
FIG. 7 is a cross-sectional view showing a peeled off state from the state of FIG. 6.

FIG. 6 and FIG. 7 show a case where the back surface of the female member 1 is used as an engagement surface. FIG. 6 shows an state engaged with the male member 1. FIG. 7 shows a peeled-off state. The female member 1 is used in a way that the surface thereof being adhered onto an outer member such as an absorbent article. The rib portions 4 and the grooves 5 are formed in the surface of the female member 1. Accordingly, the surface thereof is not entirely adhered. For this reason, FIGS. 6 and 7 show behaviors having same tendency as those of FIG. 4 and FIG. 5 in which the surface is used as the engagement surface. At the time of peeling off, elastic deformation is caused as shown in FIG. 7. Accordingly, even if bending or impulsive force such as an abdominal pressure occurs, the female member 1 is not peeled off from the engaged state.

Figure 8:
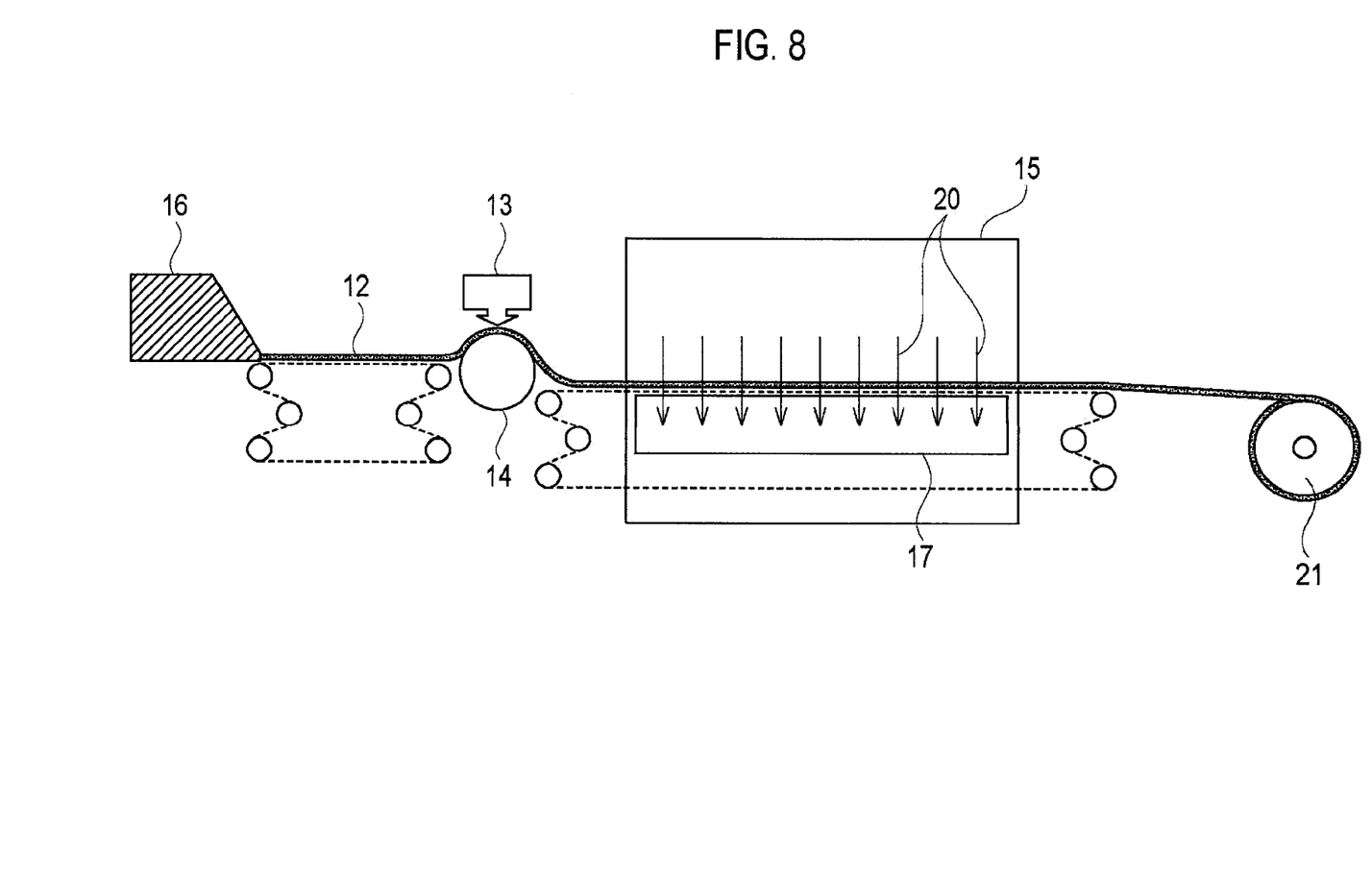
FIG. 8 is a side view of a manufacturing apparatus for manufacturing a female member.
Figure 9:
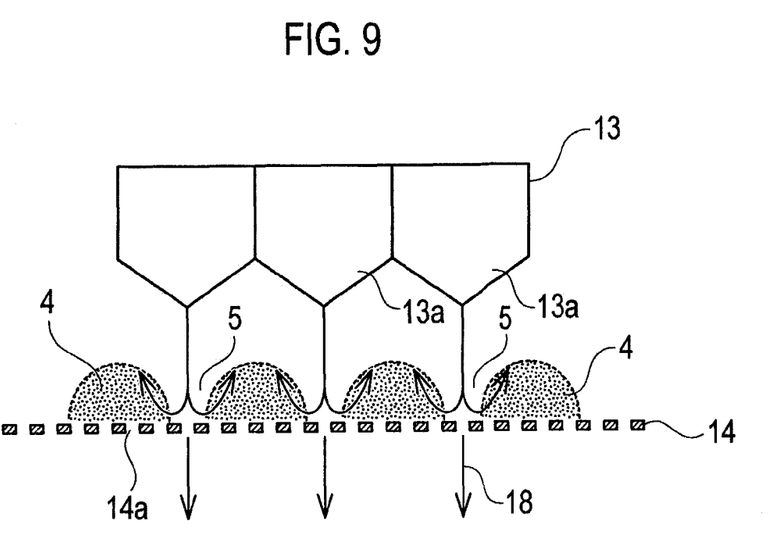
FIG. 9 is a cross-sectional view of a hot air jet nozzle portion in the manufacturing apparatus of FIG. 8.

FIG. 8 shows an apparatus used for manufacturing the female member 1 according to the present embodiment. FIG. 9 shows a portion in the apparatus of FIG. 8 in which the rib portion 4 and the groove 5 are formed.

In FIG. 8, reference numeral 12 is a fiber web to be a material for the female member 1. The fiber web 12 passes through a passage in which a hot air jet nozzle 13, an aperture plate drum 14, and a hot blast heater 15 are arranged from the upstream to the downstream. The hot blast heater 15 is provided with an aspirator 17.

Reference numeral 16 is a card for forming the fiber web 12. The fiber web 12 is formed by a normal method using the card 16, and then the fiber web 12 is brought into contact with the aperture plate drum 14. As shown in FIG. 9, the aperture plate drum 14 has a number of holes 14a, and sucks the fiber web 12 in the direction shown by an arrow 18 through the holes 14a. The hot air jet nozzle 13 is located above the aperture plate drum 14 and ejects hot air jet from multiple nozzles 13a arranged with a predetermined pitch in the CD direction onto the fiber web 12. On this aperture plate drum 14, the fiber web 12 is sucked from the lower surface thereof, while hot air jet with a temperature of +50° C. to −50° C. from the melting point of the fibrous material is blown out of the nozzles 13a onto the upper surface of the fiber web 12.

The fibrous material in a portion onto which the hot air jet is blown is removed to the both sides of the portion, and thus the groove 5 is formed in the removed portion and the rib portion 4 is formed in such a manner that the removed fibrous material is vault piled in a vault shape between the adjacent nozzles 13a.

In this manner, after the fibrous web 12 passes through the hot air jet nozzle 13, the rib portion 4 and the groove 5 are formed therein, which results in a processed web 19. This processed web 19 is led into the hot blast heater 15 with the fibrous material being in a semifused state. Similar to a case of a general air-through nonwoven, hot blast 20 with a temperature of 130° C. to 160° C. is blown thereonto. Thereby, the fibrous material is in a fully fused state and then is rolled up by the roller 21 to finish the manufacturing process.

In the above-described manufacturing process, by giving the shape of a waveform synchronized with the hot air jet nozzle 13 in the CD direction of the aperture plate drum 14, the rib portions 4 and the grooves 5 can be formed on both sides of the web. In addition, if the aperture 6 (see, FIG. 2 and FIG. 3) is formed in the groove 5, the aperture 6 can be formed by sparsely arranging portions without the aperture 14a with a predetermined interval on a line in the aperture plate drum 14 in which the hot air jet is ejected. The apertures 6 are formed in the portions without the holes 14a.

Figure 10:
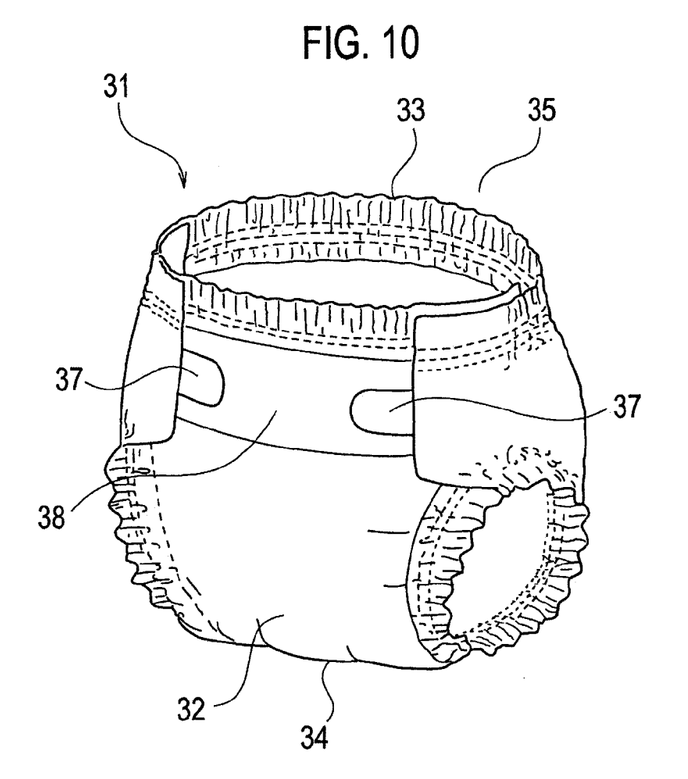
FIG. 10 is a perspective view showing one embodiment of an absorbent article of the present invention.

FIG. 10 shows one embodiment of the absorbent article 31 of the present invention. The absorbent article 31 is an development type disposable diaper in which an outer member 35 is formed by a front waistline member 32, a back waistline member 33, and an inseam member 34 formed between the waistline members 32 and 33. The inseam member 34 includes an absorber 36 integrally provided inside thereof. The absorber 36 is liquid permeable and the outer member is liquid impermeable.

The back waistline member 33 is to overlap the front waistline member 32 and has male members 37 respectively attached on both edge portions in the width direction. In contrast, the front waistline member 32 has a belt-like female member 38 attached on the outer upper surface thereof. When the male member 37 engages with the female member 38, the diaper is in a used state. In this case, the female member 38 may be attached to entirely cover the front waistline member 32.

With the use of the female member 1 shown in FIG. 1 to FIG. 3 as the female member 38 of the absorbent article 31, the female member 38 and the male member 37 are preferably engaged. Accordingly, the engagement is not released even when the diaper is deformed or instantaneous impulsive force acts thereon.

Figure 11:
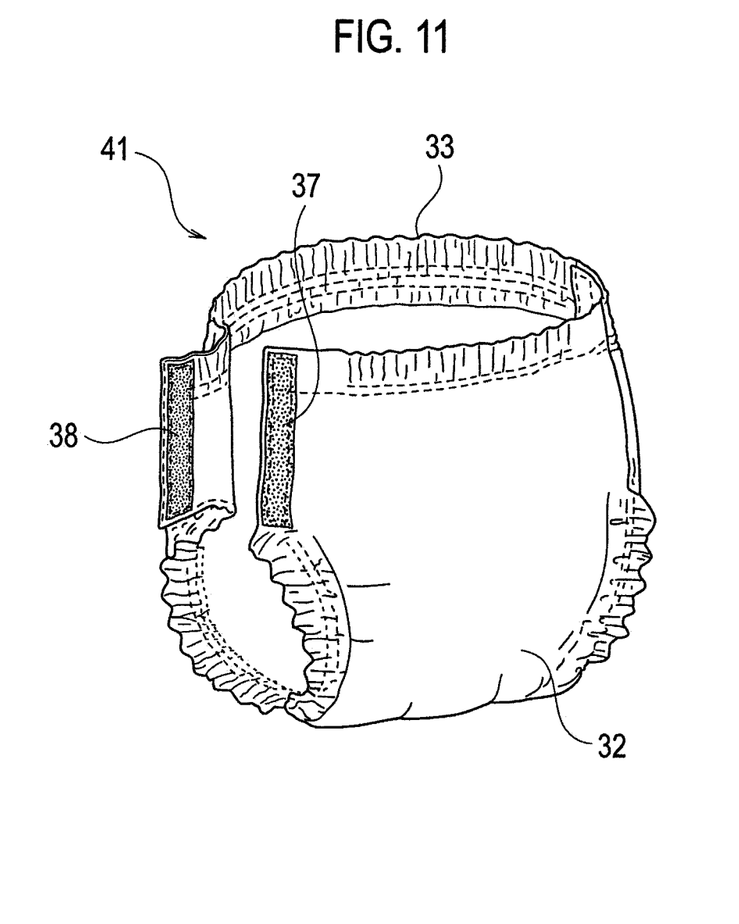
FIG. 11 is a perspective view showing a state where a hook-and-loop fastener is unfastened.

FIG. 11 shows another absorbent article 41, in which same reference numerals are given and corresponded to the same member as those of FIG. 10. The hook-and-loop fastener formed of the female member and the male member is attached to the front waistline member 32 and the back waistline member 33 in the width direction of the hook-and-loop fastener. The engagement of the hook-and-loop fastener makes an underpants shape as a whole. The male member 37 is attached to the marginal outer surface of the front waistline member 32. In addition, the female member 38 is attached to the marginal inner surface of the back waistline member 33. When the female member 38 and the male member 37 are engaged, an underpants shape is held. In this absorbent article 41, the use of the female member 1 shown in FIG. 1 to FIG. 3 as the female member 38 can prevent inadvertent release of the engagement with the male member 37.

Further, in the absorbent article 41 with this structure, the female member 38 is placed on a body side of a wearer. However, the female member 38 has the structure including the rib portions 4 and the grooves 5, and is soft and excellent in liquid penetration and air permeability. Accordingly, even when the female member 38 is arranged in this position, it does not hurt the wearer.

Note that, in the above-described embodiment, the female member 38 is used for one portion of the absorbent article 31, which is a disposable diaper, but at least one of the front waistline member 32 and the back waistline member 33 may be formed by the above-described female member 38.

DESCRIPTION OF EMBODIMENTS

Table 1 shows characteristics of fiber to be used for example 1 and comparative examples 1 and 2.
(Manufacturing Method)

Fibers having the compounding ratios of table 1 are supplied to a manufacturing apparatus shown in FIG. 8 and FIG. 9 to manufacture a female member (nonwoven) of a hook-and-loop fastener. Manufacturing was conducted under the following conditions. Specifically, four nozzles 13a, each having the hole diameter of 1.0 mm and the pitch of 50 mm, are arranged, hot air jet with the temperature of 150° C. and an air volume of 0.12 $m^3$/min/$m^2$ is then blown from the hot air jet nozzles 13, and hot blast 20 with the temperature of 150° C. and an air volume of 15 $m^3$/min/$m^2$ is thereafter blown in the hot blast heater 15 for approximately 10 seconds. Thereby, the air through nonwoven according to the example 1, having a surface with a basis weight in 35 g/$m^2$, a pitch of the rib portions 4 in 5 mm, and a width of the groove 5 in 1.3 mm, is obtained. In this case, the groove 5 has apertures 6 formed with the pitch of 5 mm in the MD direction.

On the other hand, air through nonwovens according to comparative examples 1 and 2 are manufactured at the compounding ratios shown in table 1 under the same conditions as those of example 1. Comparative example 1 is manufactured without the hot air jet being blown from the hot air jet nozzle 13. Comparative example 2 is manufactured by changing the air volume condition of the hot air jet in example 1 to 10 $m^3$/min./$m^2$. Comparative example 2 is a nonwoven thicker than example 1.
(Evaluation)

Evaluation is made for peel strength, fluff, holding power, and engagement stickiness using male members all having the same structure which is to be engaged with example 1 and comparative examples 1 and 2 in the MD direction. Results are shown in table 2. The thicknesses are shown in table 1. An evaluation method will be described below.
[Thickness Measurement]

A sample of 10 cm square is measured with the load of 3 g/$cm^2$ by using a thickness gauge (product name "PEACOK DIAL THICKNESS GAUGE No.CI1352").
[135° Peel Test]

The nonwoven which is a female member is cut into a test piece of 3 to 5 cm×5 cm. This test piece is bonded to a 5 cm×8 cm spunbonded nonwoven (20 to 30 g/$cm^2$) with a two-sided adhesive tape so as not to be peeled off and this is used as a female member sample 53. In contrast, a 2 cm×3 cm male member is bonded to a 12 cm×3 cm spunbonded nonwoven (20 to 30 g/$cm^2$) with a two-sided adhesive tape so as not to be peeled off and this is used as a male member sample 56.

The female member sample 53 is bonded to a 6 cm×10 cm stainless plate with a two-sided adhesive tape so as not to be creased. Thereafter, the male member sample 56 is placed on the female member sample 53. Then, a 700 g roller reciprocates once thereon at a rate of 300 mm/min, so that the test piece (female member) and the male member are engaged. After that, a 500 g load is put on the engaged male member sample 56 from its one end for three seconds so that shearing force would act on the engagement surface. Note that, the width of the roller is 45 mm and the diameter thereof is 95 mm, and a tape pressure roller of Tester Sangyo Co., Ltd. is used.

Figure 12:
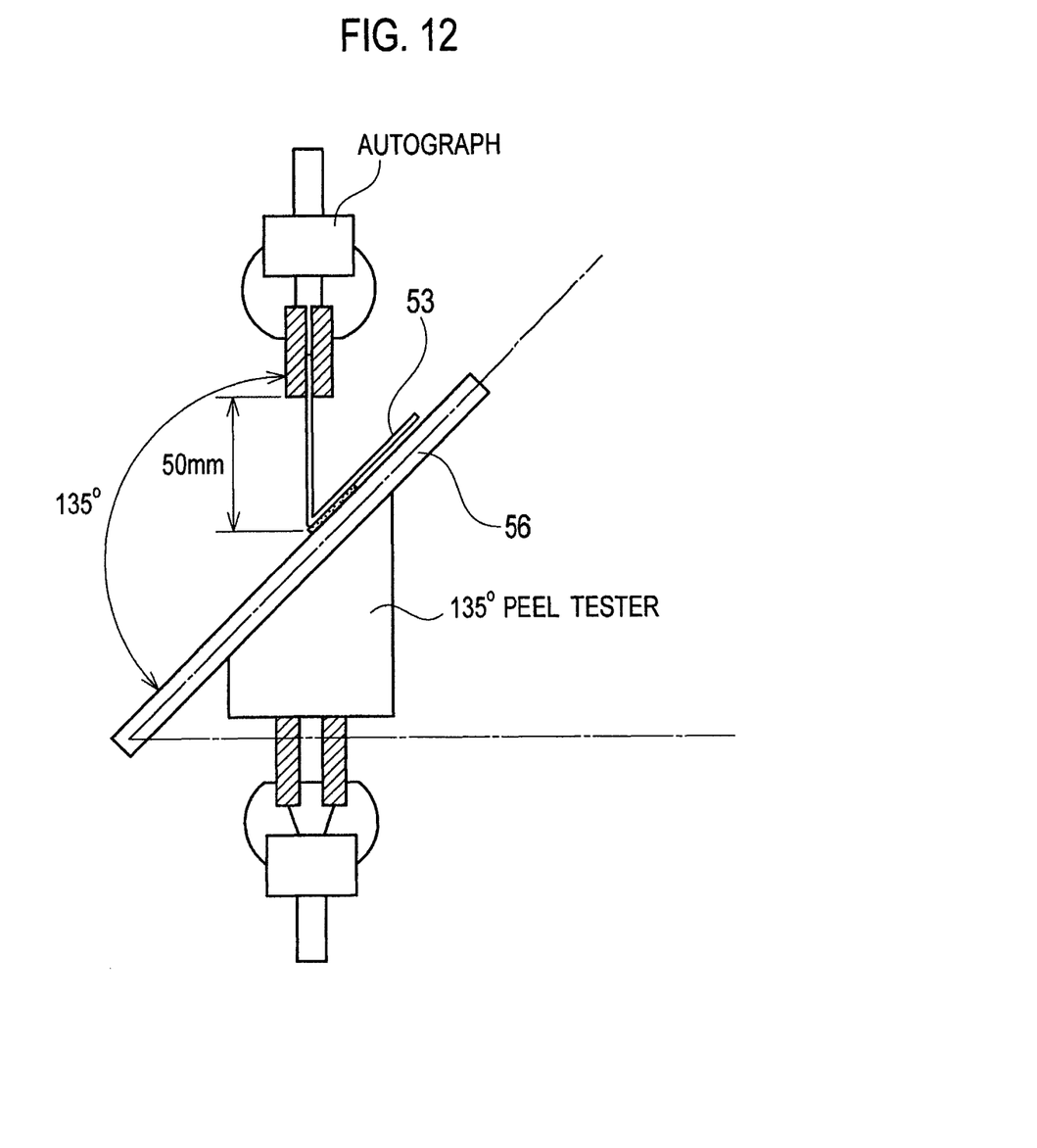
FIG. 12 is a front view of 135° peel tester.

FIG. 12 shows a 135° peel tester in which the above-described stainless plate is attached to an autograph and the male member sample 56 is pulled from one end thereof and to be peeled off so that a peeling angle between the female member sample 53 and the male member sample 56 is to be 135°. Force needed for this peeling is set to be 135° peeling force.

Conditions for the autograph are set as follows.

Measurement conditions: load cell=5 kg, a pulling rate=300 mm/min Between an upper side zipper and a sample=50 mm (in vertical direction)
[Holding Power Test]

Figure 13:
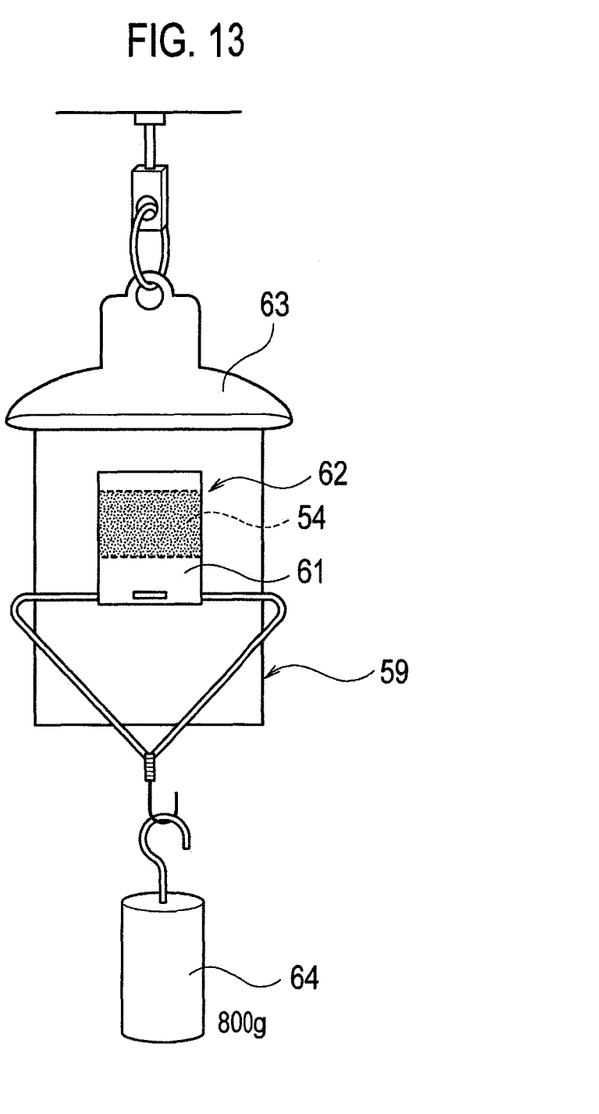
FIG. 13 is a front view of a holding power tester.

A female member sample 59 to be used for a holding power test as shown in FIG. 13 is made by bonding a 5 cm×5 cm female member 61 to a 10 cm×10 cm spunbonded nonwoven (20 to 30 g/$cm^2$) with a two-sided adhesive tape so as not to be peeled off. In addition, a male member sample to be used for the holding power test is made by bonding a 2 cm×4 cm male member 54 to a 4 cm×8 cm spunbonded nonwoven (20 to 30 g/$cm^2$) with a two-sided adhesive tape so as not to be peeled off.

The above-described male member sample is placed on the female member sample 59. Thereafter, a 700 g roller reciprocates once thereon at a rate of 300 mm/min so that the male member 54 and the female member 61 are engaged. Then, this sample is left under conditions of 20° C. and 60% RH for 30 minutes.

FIG. 13 shows a holding power tester in a state where the upper end of the female member sample 59 is suspended by a fastening device 63. The holding power tester in this state is left in an atmosphere of 40° C. with an 800 g weight 64 being suspended at the lower end of the male member sample 62. Then, time until the weight 64 falls when the engagement is peeled off, is measured. This time is set to be holding power. In this case, if the weight 64 does not fall even after 60 minutes, the maximum holding power is set to be 60 minutes.
[Engagement Stickiness Test]

Figure 14:
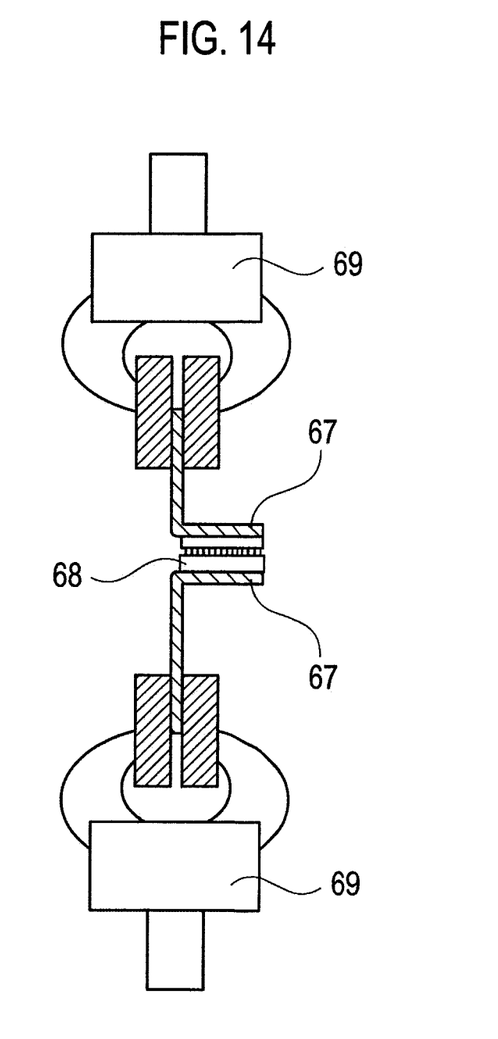
FIG. 14 is a front view showing an engagement stickiness tester.

A female member sample used for an engagement stickiness test FIG. 14 is made by sticking a 2 cm×4 cm female member on a 3 cm×5 cm spunbonded nonwoven (20 to 30 g/$cm^2$) with a two-sided adhesive tape so as not to be peeled off. The size of a male member used for the engagement stickiness test is 1.5 cm×3 cm and a two-sided adhesive tape is stuck on the back surface thereof. This male member is placed on the female member sample. Then, a 700 g roller reciprocates once thereon at a rate of 300 mm/min, so that the male member and the female member are engaged.

FIG. 14 shows an engagement stickiness tester in which a sample 68 having the male member and the female member being engaged is sandwiched between two of upper and lower L-shaped metal fittings (weight of 13.5 g) 67 and is attached on the upper and lower L-shaped metal fittings 67 with a two-sided adhesive tape. Thereafter, the upper and lower L-shaped metal fittings 67 are attached to the upper and lower autographs 69 so as to measure engagement stickiness force. The measurement is done by setting a displacement distance at the maximum loading to be "maximum displacement."

TABLE 1

| | USED FIBER AND COMPOUNDING RATIO | BASIS WEIGHT | THICKNESS (mm) |
|---|---|---|---|
| EXAMPLE 1 | PET/PE 3.3 dt × 38 mm 85% 2.6 dt × 38 mm 15% | 35 | 1.53 |
| COMPARATIVE EXAMPLE 1 | | | 0.77 |
| COMPARATIVE EXAMPLE 2 | | | 1.55 |

TABLE 2

| | ENGAGEMENT SURFACE | PEEL STRENGTH 135° PEEL (N) | | | | | FLUFF | HOLDING POWER (MINUTE) | | ENGAGEMENT STICKINESS (mm × N) |
| | | FIRST TIME | SECOND TIME | THIRD TIME | FOURTH TIME | FIFTH TIME | | A | B | |
|---|---|---|---|---|---|---|---|---|---|---|
| EXAMPLE 1 | FRONT SURFACE | 1.41 | 1.39 | 1.18 | 1.12 | 1.18 | ○ | 51 | 42 | 25.4 |
| | BACK SURFACE | 0.73 | 0.90 | 1.01 | 0.84 | 0.88 | NON | 31 | 59 | 19.4 |
| COMPARATIVE EXAMPLE 1 | FRONT SURFACE | 0.75 | 0.72 | 0.76 | 0.73 | 0.69 | ○ | 2 | 6 | 5.1 |
| COMPARATIVE EXAMPLE 2 | FRONT SURFACE | 1.10 | 1.24 | 0.93 | 0.80 | — | BROKEN | 1 | 0 | 62.7 |

FLUFF EVALUATION = NONE ○ = A LITTLE = MORE OR LESS X = FAIRLY

HOLDING POWER

A = HOLDING POWER OF AN ARTICLE IN THE FIRST PEEL TEST

B = HOLDING POWER OF AN ARTICLE IN THE FIFTH PEEL TEST

As shown in table 2, with regard to both the front surface and back surface of the female member of example 1, all results on peel strength of the first to fifth 135° peel tests, on fluff, on the holding power test, and on the engagement stickiness test are preferable. In example 1, on the back surface, the result of the holding power in the fifth peel test is higher than the holding power in the first peel test. The reason is that engagement force is increased because the thickness of the female member is recovered by repeating the peel test.

In contrast, in comparative example 1, peel strength and fluff are preferable, while the holding power test and the engagement stickiness test are not preferable. In comparative example 2, the sample is peeled off and broken at the fifth peel test. Accordingly, the female members according to comparative examples 1 and 2 are not on a level as a preferable female member. Here, the broken state is such that connection of the material itself is released in the Z direction (thickness direction) and the material is peeled off having the male member stuck thereon in a layered state.

Figure 15:
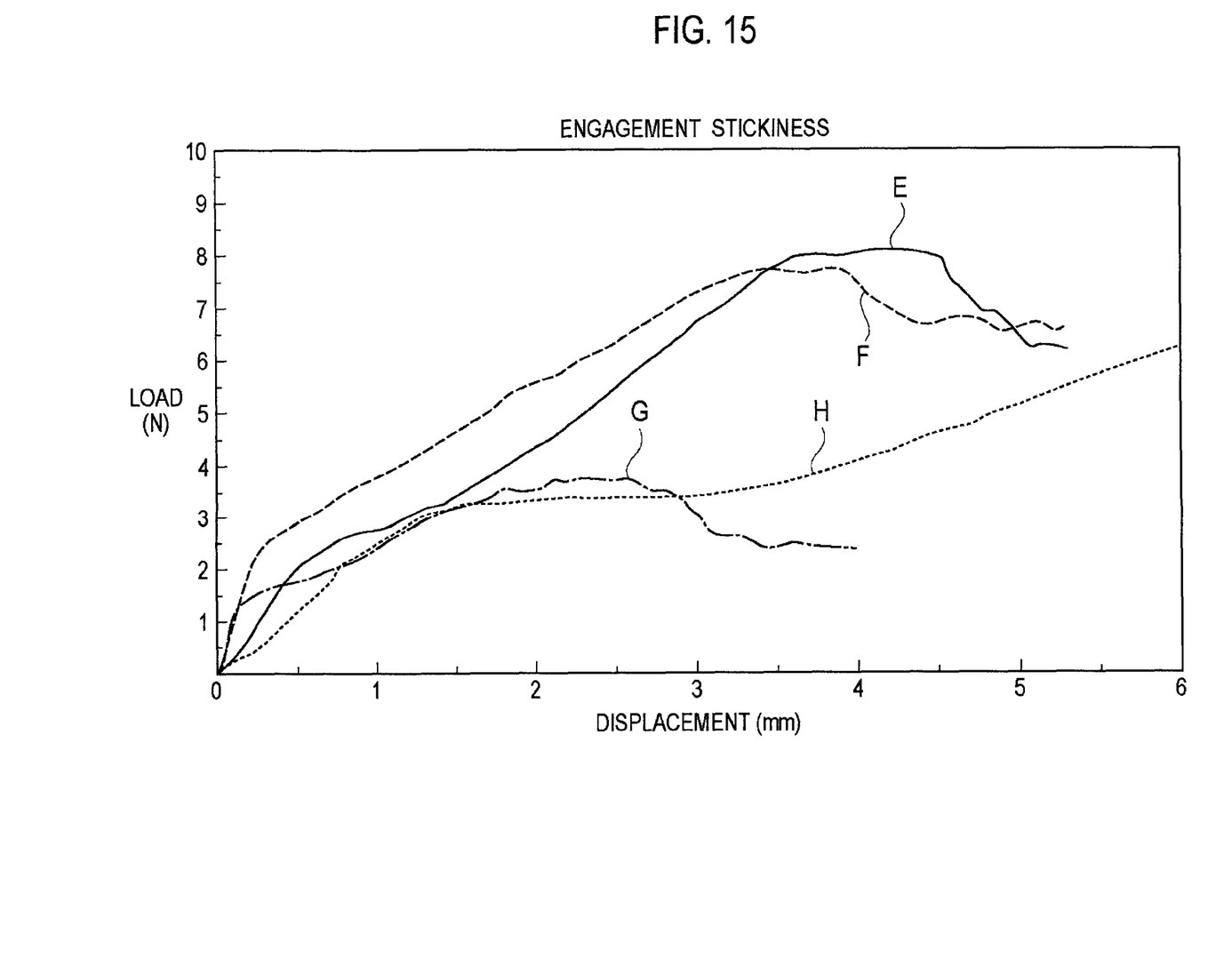
FIG. 15 is a characteristic view showing the engagement stickiness in relation to peeling action.

FIG. 15 shows a characteristic view of the engagement stickiness in the peel test. A curve E shows the engagement stickiness on the front surface of example 1 and a curve F shows the engagement stickiness on the back surface of example 1. A curve G shows the engagement stickiness of the front surface of comparative example 1 and a curve H shows the engagement stickiness of the front surface of comparative example 2. In example 1, both the front surface and the back surface have large stickiness.

This application is based upon and claims the benefit of priority from the prior Japanese Patent Application No. JP 2008-056903, filed on Mar. 6, 2008; the entire contents of which are incorporated herein by reference.

INDUSTRIAL APPLICABILITY

As described above, according to a female member of a hook-and-loop fastener of the present invention, elastic deformation in which a height is increased as a width is narrowed is caused when a dense fiber portion in which a fibrous material has a high basis weight is elongated in a thickness direction. Accordingly, engagement with a male member gains stickiness, which results in preferable engagement with the male member. As a result, an absorbent article, such as a disposable paper diaper, a sanitary napkin, a pantiliner is available.

The invention claimed is:

1. A female member of a hook-and-loop fastener formed of a fibrous material, the female member engageable with a mating male member, the female member comprising:
   a plurality of lines of dense fiber portions in which the fibrous material has a high basis weight; and
   a plurality of lines of sparse fiber portions provided between the dense fiber portions, the fibrous material in the sparse fiber portions having a basis weight lower than in the dense fiber portions, and
   wherein the dense fiber portions are continuous convex ribs which are formed on the fibrous material being piled up, and the sparse fiber portions are continuous concave grooves provided between the ribs.

2. The female member of a hook-and-loop fastener according to claim 1, wherein each of the ribs has a thickness of 0.3 mm to 0.6 mm, and a pitch between the lines of the ribs is 2 mm to 15 mm.

3. The female member of a hook-and-loop fastener according to claim 1, wherein the fibrous material is piled on a base layer portion having a thickness of the fibrous material underlying the grooves so as to form the ribs, and a volume of the fibrous material piled on the base layer portion is equivalent to a volume inside the grooves.

4. The female member of a hook-and-loop fastener according to claim 1, wherein the sparse fiber portions have a plurality of apertures passing through from a front surface to a back surface formed to be arrayed in a line direction of the ribs.

5. The female member of a hook-and-loop fastener according to claim 1, wherein the fibrous material continues from a back surface side to a front surface side in a thickness direction of the fibrous material in a state where fibers constituting the fibrous material interlaced with one another.

6. A hook-and-loop fastener, comprising:
a male member including an engagement surface formed of groups of a plurality of projection; and
the female member according to claim 1, engageable with the engagement surface.

7. An absorbent article which is formed of an outer member including a front waistline member, a back waistline member, and an inseam member, and of an absorber integrally provided to the inseam member, the absorbent article comprising:
a hook-and-loop fastener formed of a male member and the female member according to claim 1, the male member being provided to at least one of the front waistline member and the back waistline member and including an engagement surface, the female member according to claim 1 being provided to the other one of the front waistline member and the back waistline member and engageable with the engagement surface.

8. The absorbent article according to claim 7, wherein
edge portions on both sides of the front waistline member are respectively joined to edge portions on both sides of the back waistline member, in advance, by joining hook-and-loop fasteners arranged on the edge portions on the both sides of the front waistline member and the edge portions on the both sides of the back waistline member in advance, which causes the absorbent article to have an underpants shape as a whole.

9. An absorbent article which is formed of an outer member including a front waistline member, a back waistline member, and an inseam member, and of an absorber which is integrally provided to the inseam member, wherein at least one of the front waistline member and the back waistline member is formed of the female member of a hook-and-loop fastener according to claim 1.

10. The female member of a hook-and-loop fastener according to claim 1, wherein the dense fiber portions and the sparse fiber portions continue in a conveyance direction in a manufacturing process.

* * * * *